(12) United States Patent
Miernik et al.

(10) Patent No.: US 12,193,737 B2
(45) Date of Patent: Jan. 14, 2025

(54) SYSTEM FOR MONITORING TEMPERATURE WHILE INTRACORPORAL LASER LITHOTRIPSY IS BEING CARRIED OUT

(71) Applicant: GYRUS ACMI, INC, Westborough, MA (US)

(72) Inventors: Arkadiusz Miernik, Freiburg (DE); Simon Hein, Freiburg (DE); Ralf Petzold, Freiburg (DE)

(73) Assignee: Gyrus ACMI, Inc., Westborough, MA (US)

( * ) Notice: Subject to any disclaimer, the term of this patent is extended or adjusted under 35 U.S.C. 154(b) by 365 days.

(21) Appl. No.: 17/625,801

(22) PCT Filed: Jul. 7, 2020

(86) PCT No.: PCT/EP2020/069125
§ 371 (c)(1),
(2) Date: Jan. 10, 2022

(87) PCT Pub. No.: WO2021/005060
PCT Pub. Date: Jan. 14, 2021

(65) Prior Publication Data
US 2022/0257319 A1    Aug. 18, 2022

(30) Foreign Application Priority Data
Jul. 11, 2019 (DE) .................. 202019103823.3

(51) Int. Cl.
*A61B 18/26* (2006.01)
*A61B 18/00* (2006.01)

(52) U.S. Cl.
CPC .... *A61B 18/26* (2013.01); *A61B 2018/00005* (2013.01); *A61B 2018/00648* (2013.01);
(Continued)

(58) Field of Classification Search
CPC .......... A61B 18/26; A61B 2018/00005; A61B 2018/00648; A61B 2018/00678;
(Continued)

(56) References Cited
U.S. PATENT DOCUMENTS

| 5,025,778 A | 6/1991 | Silverstein et al. |
| 6,347,251 B1 * | 2/2002 | Deng ................. A61B 18/1477 606/41 |

(Continued)

FOREIGN PATENT DOCUMENTS

| CN | 114269276 | 6/2024 |
| CN | 114269276 B | 6/2024 |

(Continued)

OTHER PUBLICATIONS

International Search Report for International Application No. PCT/EP2020/069125, dated Sep. 14, 2020; 10 pages.

(Continued)

*Primary Examiner* — Scott M. Getzow
(74) *Attorney, Agent, or Firm* — Schwegman Lundberg & Woessner, P.A.

(57) ABSTRACT

A system for monitoring temperature when carrying out laser light-based lithotripsy in which includes an endoscopic assembly comprising a working channel for a fiber optic cable which is optically coupled to a laser on a proximal side and include a light exit aperture on a distal side, and an irrigation fluid channel opening into a region of the light exit aperture on the distal side which is in fluid communication with an irrigation fluid reservoir on the proximal side. The system includes a modular unit including a flow sensor, which determines the irrigation flow rate without coming into contact with the irrigation fluid; input, via which operating parameters of the laser can be determined, can be transmitted to a processor connected to the input; a tem- (Continued)

perature sensor which determines the temperature of the irrigation fluid without coming into contact with the irrigation fluid; an analyzer, which numerically determines the temperature of the irrigation fluid and the determined applied laser power, and the temperature generated intracorporeally during the laser lithotripsy at the location of the light exit aperture, and a comparator, which produces a signal in the event that a threshold value is exceeded.

20 Claims, 1 Drawing Sheet

(52) U.S. Cl.
CPC ............ *A61B 2018/00678* (2013.01); *A61B 2018/00702* (2013.01); *A61B 2018/00732* (2013.01); *A61B 2018/00791* (2013.01); *A61B 2018/00863* (2013.01); *A61B 2018/0094* (2013.01); *A61B 2018/00982* (2013.01); *A61B 2218/002* (2013.01)

(58) Field of Classification Search
CPC .......... A61B 2018/00702; A61B 2018/00732; A61B 2018/00791; A61B 2018/00863; A61B 2018/0094; A61B 2018/00982; A61B 2218/002; A61B 2018/00642; A61B 1/00006; A61B 1/128; A61B 1/307; A61B 18/22; A61B 2018/0066; A61B 2018/263; A61B 1/12
See application file for complete search history.

(56) References Cited

U.S. PATENT DOCUMENTS

| | | | | |
|---|---|---|---|---|
| 9,956,040 | B1* | 5/2018 | Lastarria | A61B 18/22 |
| 2005/0197536 | A1* | 9/2005 | Banik | A61B 1/0016 |
| | | | | 600/179 |
| 2008/0259970 | A1* | 10/2008 | Vogler | H01S 3/0941 |
| | | | | 372/6 |
| 2014/0276687 | A1* | 9/2014 | Goodman | A61B 18/24 |
| | | | | 606/33 |
| 2017/0325673 | A1* | 11/2017 | Traxer | A61B 1/307 |
| 2018/0055568 | A1* | 3/2018 | Shelton | A61M 3/0202 |
| 2018/0206911 | A1 | 7/2018 | Christian et al. | |

FOREIGN PATENT DOCUMENTS

| | | |
|---|---|---|
| DE | 202017102316 U1 | 5/2017 |
| EP | 3996619 | 8/2023 |
| IN | 202247001246 | 2/2022 |
| IN | 202448043269 | 6/2024 |
| IN | 202448043269 A | 6/2024 |
| JP | S5623943 | 3/1981 |
| JP | 2001079016 | 3/2001 |
| JP | 2018118115 | 8/2018 |
| WO | 2018109139 | 6/2018 |
| WO | 2021005060 | 1/2021 |

OTHER PUBLICATIONS

"International Application Serial No. PCT EP2020 069125, Written Opinion mailed Oct. 9, 2020", 9 pgs.
"International Application Serial No. PCT EP2020 069125, International Preliminary Report on Patentability mailed Jan. 20, 2022", 12 pgs.
"Indian Application Serial No. 202247001246, First Examination Report mailed Dec. 4, 2023", 5 pgs.
"Chinese Application Serial No. 202080057106.9, Office Action mailed Oct. 31, 2023", with English Translation, 18 pgs.
"European Application Serial No. 23189494.0, Extended European Search Report mailed Dec. 19, 2023", 12 pgs.
"Japanese Application Serial No. 2022-501171, Notification of Reasons for Refusal mailed Jan. 9, 2024", with machine translation, 6 pgs.
"Chinese Application Serial No. 202080057106.9, Response filed Mar. 26, 2024 to Office Action mailed Oct. 31, 2023", with English claims, 20 pgs.
"Japanese Application Serial No. 2022-501171, Response filed Apr. 9, 2024 to Notification of Reasons for Refusal mailed Jan. 9, 2024", W English Claims, 10 pgs.
"Indian Application Serial No. 202247001246, Response filed Jun. 4, 2024 to First Examination Report mailed Dec. 4, 2023", 9 pgs.

* cited by examiner

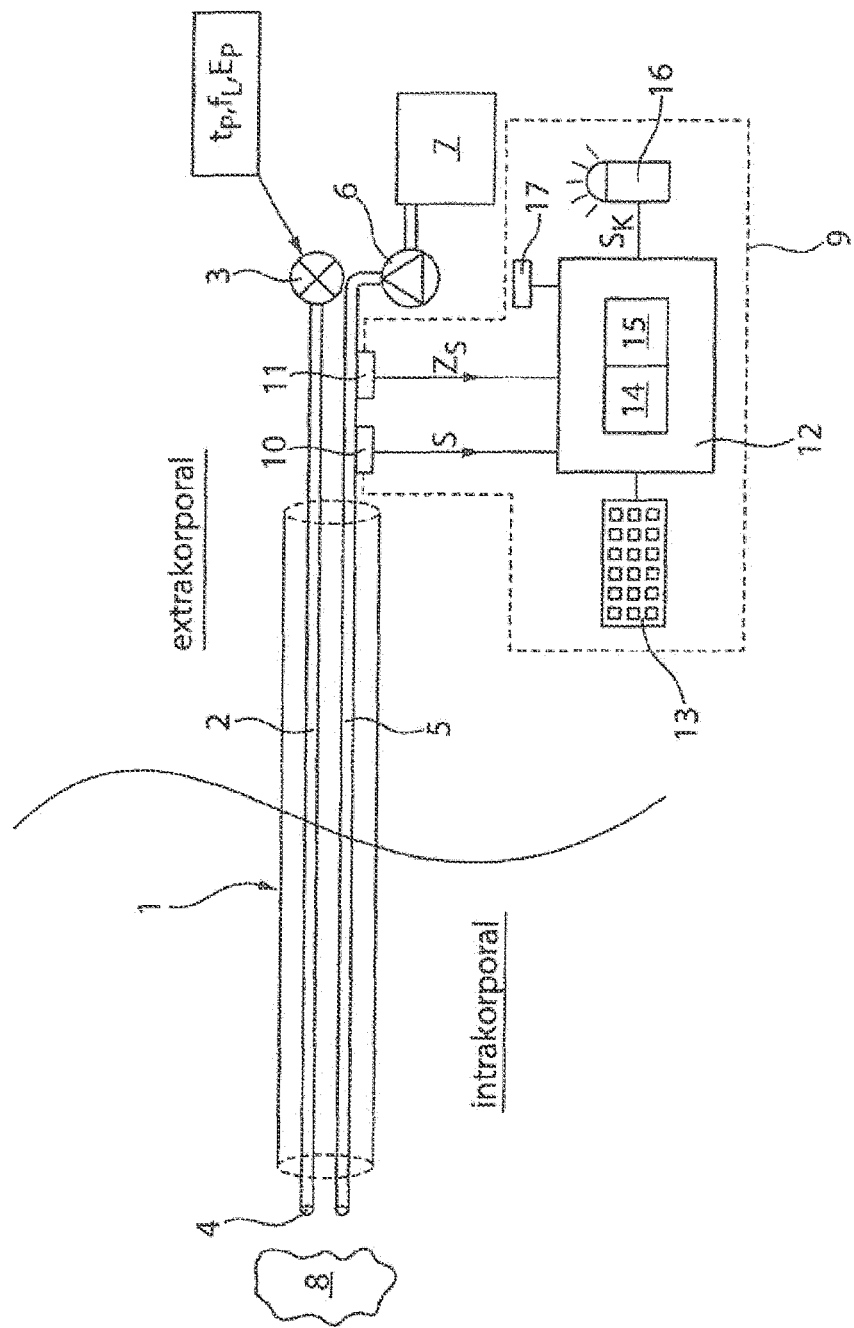

SYSTEM FOR MONITORING TEMPERATURE WHILE INTRACORPORAL LASER LITHOTRIPSY IS BEING CARRIED OUT

CROSS-REFERENCE TO RELATED APPLICATIONS

This application claims priority from International Patent Application No. PCT/EP2020/069125 filed Jul. 7, 2020, which claims priority from German Application No. 20 2019 103 823.3 filed Jul. 11, 2019, which are hereby incorporated herein by reference in their entirety.

BACKGROUND OF THE INVENTION

Field of the Invention

The invention relates to a system for monitoring temperature when carrying out laser light-based intracorporeal lithotripsy, in which an endoscopic assembly is employed which comprises a working channel for a fiber optic cable, which is optically coupled to a laser on the proximal side and has a light exit aperture on the distal side, as well as an irrigation fluid channel which opens into the region of the light exit aperture on the distal side and is in fluid communication with an irrigation fluid reservoir on the proximal side.

DESCRIPTION OF THE PRIOR ART

Intracorporeal lithotripsy is a minimally-invasive surgical method for shattering stone concretions, for example gallstones, urinary stones or kidney stones, which primarily collect in excretory ducts in the affected organs and can cause severe pain as well as other medical problems. Of the many known intracorporeal lithotripsy procedures, laser-induced lithotripsy has become an established procedure, during which high energy laser beams are applied via a fiber optic cable to the location of a stone to be shattered in the form of laser pulses. The interaction of the laser pulse with the intracorporeal medium forms a bubble of vapor which pulse-like expansion generates pressure waves which lead to fragmentation of the stone. Depending on their size, the fragments of stone generated by laser-induced lithotripsy can be excreted naturally or they can be extracted with suitably configured endoscopic gripping tools.

Endoscopes are used to carry out laser-based lithotripsy which have at least one working channel for a fiber optic cable which is optically coupled to a laser on the proximal side and have a light exit aperture on the distal side. In order to be able to follow the organic access routes to the stones with the endoscope and to burden patients as little as possible during the treatment, endoscopes of this type may be pliable and flexible in configuration. In addition, an irrigation fluid can be applied via endoscopes of this type, usually via a working channel which opens into the region of the light exit aperture on the distal side and is in fluid communication with an irrigation fluid delivery device on the proximal side, preferably in the form of at least one of an irrigation syringe and a controllable or regulatable delivery pump, as well as with an irrigation fluid reservoir.

With the aid of an endoscopic assembly of this type comprising the endoscope and the aforementioned peripheral devices which are connected to it, the laser power applied intracorporeally at the location of the stone to be shattered as well as the quantity of irrigation fluid which is discharged to the irrigation channel on the distal side have to be matched to each other in a manner such that on the one hand, effective stone shattering can be carried out, and on the other hand, no local overheating of surrounding areas of tissue caused by the laser light occurs which could result in irreversible damage to the tissue. For the most part, endoscopes of this type are provided with additional glass fiber optics for the operator or an imaging sensor at the tip of the endoscope which has to be kept optically clear with the aid of a metered delivery of irrigation fluid in order to guarantee a clear view for the operator in order to monitor the shattering process.

US published patent application 2018/0055568 A1 describes an endoscopic assembly of this type for carrying out laser-based lithotripsy with an associated irrigation fluid delivery unit which can be adjusted as a function of at least one of the parameters influencing the lithotripsy process that is the irrigation flow rate is influenced as a function of the lithotripsy process. In addition to optical monitoring of the shattering process, the known endoscopic assembly is provided with a temperature sensor attached to the distal end of the endoscope which is capable of detecting the distal temperature of the fluid surrounding it, on the basis of which the irrigation fluid delivery unit is regulated in order to adjust the irrigation fluid flow rate.

Even in the case of the known medical endoscope in accordance with the publication of German application DE 20 201 7 102 316 U1, which is suitable for carrying out laser-based lithotripsy, an ambient temperature sensor is disposed at the distal region of the endoscope for the purposes of temperature measurement.

Endoscopic assemblies equipped with sensors in this manner constitute extremely complicated medical instruments which have to undergo protracted and comprehensive medico-technical certification and testing.

SUMMARY OF THE INVENTION

The invention is a system for monitoring temperature when carrying out laser light-based intracorporeal lithotripsy, in which an endoscopic assembly is employed which comprises a working channel for a fiber optic cable, which is optically coupled to a laser on the proximal side and has a light exit aperture on the distal side, as well as an irrigation fluid channel which opens into the region of the light exit aperture on the distal side and is in fluid communication with an irrigation fluid reservoir on the proximal side in such a manner that it becomes possible to carry out monitored intracorporeal lithotripsy with standard endoscopes of this type without having to spend too much money and time for medico-technical testing or certification. Measures are sought by which endoscopes, laser systems and other medico-technical devices which are already in use, such as irrigation fluid devices for passive and active irrigation which are generally suitable for laser-based lithotripsy, can be retrofitted with suitably selected components in order to be able to rule out any possible thermally induced tissue degradation in the region directly surrounding the stone shattering location.

In general, intracorporeal laser application without irrigation, in the region of the distal light exit aperture of the fiber optic cable, is only possible for short periods of less than a few seconds, otherwise without any cooling provided by the irrigation so that a critical temperature of approximately 42° C. is not reached and exceeded, beyond which the surrounding tissue would be irreversibly heat-damaged. As a result, irrigation during laser light-based lithotripsy is absolutely necessary to guarantee sufficient cooling.

A reliable numerical or theoretical relationship between the intracorporeally applied laser power, the irrigation fluid flow rate, the temperature of the irrigation fluid and an intracorporeal temperature generated during application of the laser pulse has been found based on a large number of laser-based lithotripsy experiments which have been carried out.

On the basis of this discovery, in the case of known endoscopes with at least one working channel for a fiber optic cable which is optically coupled to a laser on the proximal side and with a light exit aperture on the distal side as well as an irrigation fluid channel which may be separate to or integral with the working channel and which opens into the region of the light exit aperture on the distal side and on the proximal side is in fluid communication with an optional irrigation fluid delivery unit and an irrigation fluid reservoir, a modular unit in accordance with the invention comprises at least one flow sensor as well as at least one temperature sensor which can respectively be releasably securely attached alongside at least one of the irrigation fluid channel and a supply line which is in fluid communication with the irrigation fluid channel alongside the extracorporeal region of the endoscopic assembly. In this manner, the flow sensor is constructed and disposed such that the irrigation flow rate can be determined in a manner which is without contact with the irrigation fluid. At the same time, the temperature sensor is configured and attached alongside at least one of the irrigation fluid channel and the supply line which is in fluid communication with the irrigation fluid channel in a manner such that the irrigation fluid temperature can be determined without contact.

Furthermore, the modular unit comprises either an input means via which the operating parameters for the laser can be input and can be transmitted to a processor connected to the input, or an interface via which the operating parameters for the laser can be transferred directly. The operating parameters for the laser preferably include the laser power, whereupon the calculation of the laser power applied to the location of the light exit aperture can be computed via the laser pulse frequency as well as the individual pulse energy.

In addition, an analyzer is installed in the processor unit which, on the basis of the sensor-acquired irrigation flow rate, the sensor-acquired temperature of the irrigation fluid and the determined intracorporeally applied laser power, numerically determines a temperature which is generated intracorporeally during the laser-based lithotripsy at the location of the light exit aperture. A comparator unit is separate from or integrated into the processor and compares the determined temperature with an adjustable threshold value, for example 42° C., and produces a signal if the threshold value is exceeded.

In addition, in a preferred embodiment, a signalling unit is provided which is wirelessly connected to or hardwired to the comparator by means of which the signal produced by the comparator can be made at least one of haptically, acoustically and visually perceptible. By use of the signal unit, the physician carrying out the lithotripsy can be made aware of potential intracorporeal overheating effects so that the lithotripsy treatment can be interrupted or other measures can be taken.

The modular unit in accordance with the invention, which is preferably configured as a retrofitting set or retrofitting kit, comprises components which can be attached in a modular manner to an endoscopic assembly which is already in use without compromising the general functionality of the endoscopic assembly. Thus, the system in accordance with the invention constitutes a safety system which supports the physician when carrying out laser-based lithotripsy by which the physician receives reliable and dependable information which enables the lithotripsy procedure to be carried out effectively and in a patient-friendly manner.

The only information which is required in this regard is the current temperature of the intracorporeal irrigation fluid introduced via the endoscopic assembly by which the working channel or the irrigation fluid channel, the laser power applied at the location of the stone to be shattered, as well as the irrigation flow rate at which the irrigation fluid is introduced intracorporeally through the working channel or irrigation fluid channel at the location of the laser light application.

The sensors required for the irrigation fluid temperature and irrigation flow rate respectively constitute constructional elements which are releasably securably attached to at least one of the irrigation fluid channel and the supply line which is in fluid communication with the irrigation fluid channel which are applied in a region of the endoscopic assembly which is not introduced intracorporeally into the body. Thus, preferably, the sensor which determines the irrigation flow rate is a flow sensor in the form of an ultrasound sensor. A temperature sensor in the form of an infrared sensor is suitable for acquiring the irrigation fluid temperature.

In order to determine the temperature generated at the location of the light exit aperture of the fiber optic cable, the required operating parameters which can be specified for the laser are the laser pulse frequency as well as the individual pulse energy. These operating parameters can be supplied by use of a suitably configured input, for example a keyboard, or by a voice-operated input or by a direct interface with the laser device of the processor.

The analyzer installed in the computer unit determines the temperature T generated at the location of the light exit aperture on the basis of the following formula in the following manner:

$$T = \left(14.4 \; K * \frac{[\text{laser power } [W]]}{\left[\text{irrigation flow rate } \left[\frac{ml}{min}\right]\right]}\right) + \text{temp of irrigation fluid } [K]$$

The numerical relationship between the temperature generated intracorporeally during laser-based lithotripsy at the location of the laser light application and the applied laser power, the irrigation flow rate as well as the temperature of the irrigation fluid has been confirmed in a large number of in vitro as well as ex vivo experiments.

Although the above algorithm represents a simplified formulaic relationship, the expected intracorpolaic end temperatures at the location of stone shattering during the laser-based lithotripsy can be sufficiently precisely predicted so that local overheating, which could lead to irreversible tissue damage in the immediate surroundings of the location for the laser-based lithotripsy, can be prevented.

In the event that the laser does not have an interface for indicating the laser operation, the modular unit additionally comprises a microphone for detecting an acoustic signal indicating the operation of the laser which is transmitted to the analyzer for the purpose of signal analysis which is synchronous with the actual laser operation. In this manner, during the operation of the laser, the laser produces clearly detectable acoustic signals which can be detected with the microphone unit to be time-resolved.

Although the physician who is responsible for carrying out the lithotripsy is the sole decision-maker when carrying out the laser-based lithotripsy, in a further embodiment, the modular unit in accordance with the invention comprises an additional emergency stop switch, in addition to at least one of the acoustic, visual and haptic signal-emitting; the signal can trigger an interruption to the power supply for at least the laser source.

In a further preferred embodiment, the modular unit which can be adapted to an endoscopic assembly which additionally detects the fill level of the quantity of irrigation fluid contained in the irrigation fluid reservoir. The unit is configured as a sensor provided with at least one of the irrigation fluid reservoir and a software-based analysis algorithm implemented in the processor which determines the current fill level on the basis of the irrigation flow rate detected by the sensor and the measured time period during which a discharge of irrigation fluid occurs. The sensor signal representing the fill level or the numerically determined fill level value representing the fill level serves at least for monitoring the actual state as well as for predicting the length of time to complete emptying of the irrigation fluid reservoir or as a warning upon reaching a minimum residual quantity. The information obtained in this manner is made optically or acoustically perceptible to the physician by a suitable indication. The indication may be made by the signal unit via which the physician carries out the lithotripsy to warn of about possible intracorporeal overheating effects, or by an additional indication.

A further embodiment enables additional monitoring of the temperature of the supplied irrigation fluid. To this end, the temperature of the irrigation fluid ($T_S$) which is detected by the sensor is preferably shown as an alphanumeric value on a visual display unit. Furthermore, the measured temperature is preferably supplied to the comparator or a further comparator, whereupon in the event of the temperature of the irrigation fluid ($T_S$) going above or below a critical temperature value, a signal is produced which serves to warn the treating physician. An example, in the event of the irrigation fluid becoming too cold, is a warning to avoid the risk of the patient becoming hypothermic.

In a further possible embodiment, the irrigation fluid delivery is provided with the aid of the irrigation fluid flow rate being adjusted as a function of the temperature T generated at the location of at least one of the light exit aperture and as a function of at least one operating parameter of the laser. This makes it possible to provide active regulation of the irrigation fluid flow rate for the irrigation fluid delivery such as a pump as at least one of a function of the applied laser light power and the calculated temperatures in the invention.

The system in accordance with the invention for monitoring temperature when carrying out laser light-based lithotripsy can be used in a variety of anatomical areas, such as in the bladder, ureter or renal pelvic regions. Different modes which suit the intervention may be selected which depend on the area of application. In this regard, the system offers the choice of a prostate, bladder, ureter or renal pelvic mode which are distinguished by definable warning limits and stored characteristics. In this manner, the individual risk spectrum for the various operations can be addressed.

Thus, the system can be used in any laser-based procedure in urology, in particular in laser lithotripsy, enucleation of the prostate (HoLEP, ThuLEP), laser vaporization (PVP) and interstitial laser coagulation (ILC).)

EXAMPLES OF THE INVENTION

The single FIGURE shows an endoscope 1 with a working channel for a fiber optic cable 2 which is optically coupled to a laser 3 on the proximal side and has a light exit aperture 4 on the distal side. Furthermore, the endoscope 1 has an irrigation fluid channel 5 which opens into the region of the light exit aperture 4 on the distal side and on the proximal side is in fluid communication with a fluid delivery unit 6 as well as a fluid reservoir 7. Endoscopes are also known which combine the irrigation fluid channel 5 with the working channel for the fiber optic cable 2 in one channel. Known endoscopic assemblies of this type serve to shatter intracorporeal stones 8 during the course of laser-based lithotripsy.

The system in accordance with the invention for monitoring temperature concerns a modular unit 9 which can be combined with the extracorporeal region of the endoscopic assembly comprising the endoscope 1, the laser 3, the fluid delivery unit 6 as well as the fluid reservoir 7, a preferred embodiment, the invention is composed of the following components:

Alongside the irrigation fluid supply line 5, a flow sensor 10, preferably an ultrasound sensor, is detachably secured. Similarly, alongside the irrigation fluid channel 5 or a supply line which is in fluid communication therewith, a temperature sensor 11 for detecting the irrigation fluid temperature, which is preferably an infrared sensor, is detachably secured. The sensor signals S, Zs which are produced by the sensors 10, 11, are transmitted to a processor unit 12 in a wireless or hard-wired manner.

Furthermore, an input 13 is provided, preferably as an interface to the laser for automatic operating parameter transfer, or alternatively in the form of a manually operable keyboard by which the operating parameters for the laser 3 can be input. For the operation of the laser 3, the laser pulse frequency $f_L$ as well as the individual pulse energy EP can be specified by the operator. These operating parameters can also be supplied via the input 13 to the processor 12, on the basis of which the laser power which can be applied to the location of the light exit aperture 4 can be computed.

An analysis unit 14 is installed in the processor 12 and which, based on the operating parameters of the laser, the irrigation flow rate S as well as the temperature $Z_S$ of the irrigation fluid detected by the sensors, determines the current temperature generated at the location of the light exit aperture 4 based on the following algorithm:

$$T = \left(14.4 \; K * \frac{[\text{laser power } [W]]}{\left[\text{irrigation flow rate } \left[\frac{ml}{min}\right]\right]}\right) + \text{temp of irrigation fluid } [K]$$

Next, the determined intracorporeal temperature T is compared in a comparator unit 15 with an adjustable threshold value which is preferably $T_K=42°$ C. In the case in which the threshold value $T_K$ is exceeded, the comparator unit 15 produces a signal SK which is supplied to a signal unit 16 which can then be perceived at least one of haptically, acoustically and visually by the physician who is carrying out the lithotripsy.

In addition, a microphone unit 17 is connected to the processor unit 12, by which the activity of the laser 3 is detected which ensures that the data processed by the processor 12 and the analyzer 14 implemented therein as well as the production of a signal SK based on it is synchronous with the actual operation of the laser 3.

LIST OF REFERENCE NUMERALS

1 Endoscope
2 fiber optic cable 3 laser
4 light exit aperture
5 irrigation fluid
6 irrigation fluid delivery
7 irrigation fluid reservoir
8 stone
9 modular unit
10 flow sensor
11 temperature sensor
12 processor unit
13 input
14 analyzer
15 comparator
16 signal unit
17 microphone

The invention claimed is:

1. A system for monitoring temperature when carrying out laser light-based lithotripsy, in which an endoscopic assembly is employed which comprises a working channel for a fiber optic cable which is optically coupled to a laser on a proximal side and has a light exit aperture on a distal side, as well as an irrigation fluid channel which opens into a region of the light exit aperture on the distal side and is in fluid communication with an irrigation fluid reservoir on a proximal side, the system providing a module unit which can be combined with the endoscopic assembly, the module unit comprising the following components:
a flow sensor, which can be mounted longitudinally on at least one of the irrigation fluid channel or a supply line that is in fluid communication with the irrigation fluid channel, and which determines an irrigation flow rate in a manner without contacting the irrigation fluid;
an input means for determining operating parameters of the laser based on laser power applied at a location of the light exit aperture which are determined and transmitted to a processor connected to the input means; and
a temperature sensor, which can be mounted longitudinally on at least one of the irrigation fluid channel or a supply line that is in fluid communication with the irrigation fluid channel, and which determines irrigation fluid temperature without contact with the irrigation fluid;
wherein the processor is configured to:
determine, based on the irrigation flow rate, the temperature of the irrigation fluid and applied laser power, a temperature T generated intracorporeally during the laser light-based lithotripsy at a location of the light exit aperture;
compare the determined temperature T with a threshold value and produce a signal when the threshold value is exceeded; and
output the signal when the threshold value is exceeded.

2. The system as claimed in claim 1, wherein:
the flow sensor is an ultrasound sensor.

3. The system as claimed in claim 1, wherein:
the input includes a manually operable interface or a data interface.

4. The system as claimed in claim 1, wherein: the operating parameters of the laser are laser pulse frequency and individual pulse energy.

5. The system as claimed in claim 1, wherein:
the processor determines the temperature T generated at a location of the light exit aperture based on a relationship of:

$$T = \left(14.4K * \frac{[\text{laser power}[W]]}{\left[\text{irrigation flow rate}\left[\frac{ml}{min}\right]\right]}\right) + \text{temp of irrigation fluid}[K].$$

6. The system as claimed in claim 5, wherein: the temperature sensor is an infrared sensor.

7. The system as claimed in claim 5, wherein:
a signal output unit which provides the signal produced by the processor by one of haptical, acoustical, or visual presentation.

8. The system as claimed in claim 1, comprising:
a cooler thermally coupled to at least one of the irrigation fluid channel and to the irrigation fluid reservoir, and wherein:
the cooler is activated or controlled by the signal produced by the processor.

9. The system as claimed in claim 1, comprising:
an emergency stop switch activated in response to the signal being output.

10. The system as claimed in claim 1, comprising:
a microphone which provides a signal storing operation of the laser in which the microphone is communicatively connected to the processor.

11. The system as claimed in claim 1, wherein:
the system is configured to be retrofitted by attachment to an endoscopic assembly for carrying out laser light-based lithotripsy.

12. The system as claimed in claim 11, wherein:
the endoscopic assembly includes an extracorporeal region outside a patient when the system carries out the lithotripsy; and
the temperature sensor and the flow sensor are attached in the extracorporeal region of the endoscopic assembly alongside the irrigation fluid channel or along a supply line in fluid communication therewith.

13. The system as claimed in claim 1, wherein:
the working channel and the irrigation fluid channel are a single channel in which the optic cable is positioned along a working channel which is irrigated by the irrigation fluid.

14. The system as claimed in claim 1, comprising:
means for computing or for providing direct detection by sensors of a level of filling of irrigation fluid in the irrigation fluid reservoir and which produces at least one signal dependent on the level of filling.

15. The system as claimed in claim 14, wherein:
the means for computing comprises a sensor provided with the irrigation fluid reservoir and executes a software-based analysis algorithm implemented by the processor which determines the level of filling based on the irrigation flow rate detected by the sensors and a measured length of time during which the irrigation fluid is discharged.

16. The system as claimed in claim 14, wherein:
the signal is producible by at least one of haptical, acoustical or visual detection by the signal unit or by means of a further signal means.

17. The system as claimed in claim 1, wherein:
the temperature of the irrigation fluid is detected by the temperature sensor which is coupled to the processor which produces a second signal when the temperature of the irrigation fluid falls below or exceeds a critical temperature value.

18. The system as claimed in claim 1, wherein:
the irrigation fluid channel is connected on a proximal side to an electrically operable irrigation fluid delivery unit.

19. The system as claimed in claim 18, wherein:
the irrigation fluid channel includes means for controlling irrigation fluid flow rate as a function of the temperature generated at the light exit aperture and at least one operating parameter of the laser.

20. A system for monitoring temperature when carrying out laser light-based lithotripsy, in which an endoscopic assembly is employed which comprises a working channel for a fiber optic cable which is optically coupled to a laser on a proximal side and has a light exit aperture on a distal side, as well as an irrigation fluid channel which opens into a region of the light exit aperture on the distal side and is in fluid communication with an irrigation fluid reservoir on a proximal side, the system including a module which can be combined with the endoscopic assembly, the module comprising:
  a flow sensor, which can be attached alongside at least one of the irrigation fluid channel or a supply line, in fluid communication with the irrigation fluid channel and which determines an irrigation flow rate in a manner without contacting the irrigation fluid;
  an input means for determining operating parameters of the laser based on laser power applied at a location of the light exit aperture which are determined and transmitted to a processor connected to the input means; and
  a temperature sensor, which is attachable to at least one of the irrigation fluid channel or a supply line, in fluid communication with the irrigation fluid channel and which determines irrigation fluid temperature without contact with the irrigation fluid;
wherein the processor is configured to:
  determine, based on the irrigation flow rate, the temperature of the irrigation fluid and applied laser power, a temperature T generated intracorporeally during the laser-based lithotripsy at a location of the light exit aperture;
  compare the determined temperature T with a threshold value and produce a signal when the threshold value is exceeded; and
  output the signal when the threshold value is exceeded; and
wherein the processor determines the temperature T generated at a location of the light exit aperture based on a relationship of:

$$T = \left(14.4\text{K} * \frac{[\text{laser power}[W]]}{\left[\text{irrigation flow rate}\left[\frac{\text{ml}}{\text{min}}\right]\right]}\right) + \text{temp of irrigation fluid}[K].$$

\* \* \* \* \*